United States Patent [19]
Hake

[11] Patent Number: 5,256,153
[45] Date of Patent: Oct. 26, 1993

[54] HYPODERMIC NEEDLE GUARD AND METHOD TO PREVENT NEEDLE STICK INJURIES

[76] Inventor: Lawrence W. Hake, R.R. #2, Box 108, Grand Island, Nebr. 68803

[21] Appl. No.: 704,359

[22] Filed: May 23, 1991

Related U.S. Application Data

[63] Continuation-in-part of Ser. No. 317,733, Mar. 2, 1989, Pat. No. 5,019,051.

[51] Int. Cl.$^5$ .............................................. H61M 5/32
[52] U.S. Cl. ................................. 604/198; 604/263
[58] Field of Search .............. 604/110, 192, 197, 198, 604/263

[56] References Cited

U.S. PATENT DOCUMENTS

| | | | |
|---|---|---|---|
| 4,425,120 | 1/1984 | Sampson et al. | 604/198 |
| 4,631,057 | 12/1986 | Mitchell | 604/198 |
| 4,654,034 | 3/1987 | Masters et al. | 604/192 |
| 4,659,330 | 4/1987 | Nelson et al. | 604/192 |
| 4,664,653 | 5/1987 | Sagstetter et al. | 604/197 |
| 4,664,654 | 4/1987 | Strauss | 604/198 |
| 4,666,435 | 5/1987 | Braginetz | 604/198 |
| 4,668,223 | 5/1987 | Grotenhuis | 604/191 |
| 4,681,567 | 4/1987 | Masters | 604/198 |
| 4,693,708 | 9/1987 | Wanderer et al. | 604/198 |
| 4,695,274 | 9/1987 | Fox | 604/198 |
| 4,702,738 | 10/1987 | Spencer | 604/198 |
| 4,710,170 | 12/1987 | Haber et al. | 604/110 |
| 4,723,943 | 2/1988 | Spencer | 604/198 |
| 4,737,144 | 4/1988 | Choksi | 604/198 |
| 4,738,663 | 4/1988 | Bogan | 604/198 |
| 4,743,233 | 5/1988 | Schneider | 604/192 |
| 4,762,516 | 8/1988 | Luther | 604/164 |
| 4,772,272 | 9/1988 | McFarland | 604/198 |
| 4,778,453 | 10/1988 | Lopez | 604/110 |
| 4,801,295 | 7/1989 | Spencer | 604/198 |
| 4,816,022 | 3/1989 | Poncy | 604/198 |
| 4,846,679 | 4/1989 | Carrell | 604/110 |
| 4,850,994 | 7/1989 | Zerbst et al. | 604/198 |
| 4,874,383 | 10/1989 | McNaughton | 604/198 |
| 4,927,417 | 5/1990 | Moncada et al. | 604/198 |
| 4,976,702 | 12/1990 | Andrews et al. | 604/198 |
| 5,019,051 | 5/1991 | Hake | 604/198 |
| 5,106,380 | 4/1992 | Lobello | 604/198 |
| 5,156,599 | 10/1992 | Ranford et al. | 604/198 |

FOREIGN PATENT DOCUMENTS 0350186 10/1990 European Pat. Off. ..
WO90/04984 5/1990 PCT Int'l Appl. .

*Primary Examiner*—Stephen C. Pellegrino
*Assistant Examiner*—Michael Rafa
*Attorney, Agent, or Firm*—Allegretti & Witcoff, Ltd.

[57] ABSTRACT

A needle guard and a method to prevent needle stick injuries are disclosed, for use with a hypodermic syringe or other instrument with a sharp point. The needle guard, comprises a protective sleeve with a fitting, that may be used with or added to a conventional syringe and needle assembly. The interior of the fitting contains a deformable engagement means adapted to permanently engage the fitting on the syringe barrel. Prior to and during use of the needle, the sleeve remains in a retracted position covering the barrel of the syringe. After the needle has been used, the sleeve is pushed forward into its locked extended position, so that the end of the sleeve extends beyond the tip of the needle. The tip of the needle is thereby shielded, preventing accidental sticks.

22 Claims, 6 Drawing Sheets

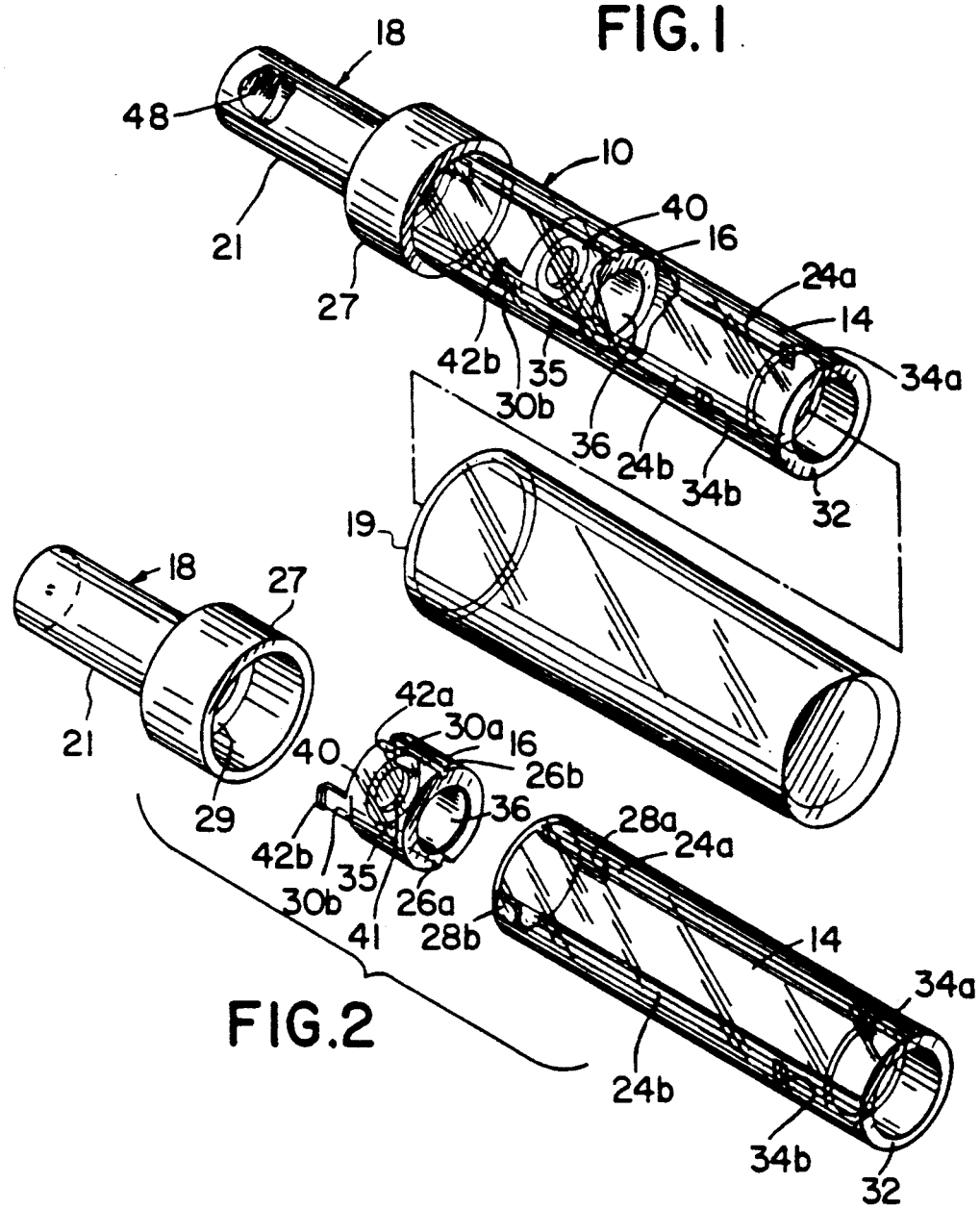

HYPODERMIC NEEDLE GUARD AND METHOD TO PREVENT NEEDLE STICK INJURIES

BACKGROUND OF THE INVENTION

This is a continuation-in-part of my earlier filed, copending patent application, Ser. No. 317,733, filed Mar. 2, 1989, now issued as U.S. Pat. No. 5,019,051.

This invention relates to syringes, and more particularly to a syringe construction designed for the prevention of needle-stick injuries.

Hypodermic syringes are widely used to inject substances into and to draw samples from human beings and animals. A hypodermic syringe typically includes a barrel that contains the substance to be injected or that is available to receive the sample to be drawn, and a needle which is connected to the barrel. Hypodermic syringes may be either reusable or disposable. Those that are disposable are normally discarded after use to avoid spread of contamination or disease.

It has been observed that there is a low but ever-present rate of needle-stick injuries suffered by medical practitioners after a syringe has been used. In one study of needle-stick injuries published recently, disposable syringes were involved in 6.9 needle-stick injuries per 100,000 items purchased, and accounted for 35 percent of the total number of needle-stick injuries from all sources. See Rates of Needle-Stick Injury Caused By Various Devices In A University Hospital, J. Jagger, M.P.H., Ph.D., E. H. Hunt, R.N., J. Brand-Elnaggar, B.A., & R. D. Pearson, M.D., 319 *New England Journal of Medicine*, 284–288, Aug. 4, 1988. The most common mechanism of injury from disposable syringes was due to attempts by hospital personnel to place a cap over the needle after use of the syringe, usually to protect themselves or others from the contaminated needle. The study concluded that efforts to implement safety guidelines have been ineffective and are unlikely to eliminate such injuries in the future. The study recommended redesign of instruments to eliminate use of needles, provide some sort of fixed barrier between the user and the needle, or allow the user's hands to remain behind the needle as it is covered.

Concern for the safety of health care workers has become acute in recent years, particularly due to the spread of the acquired immunodeficiency syndrome (AIDS). Indeed, needle-sticks by contaminated syringes have been attributed as the cause of infection in health care workers. Although an initial needle-stick injury may appear minor, the possibility of infection is serious enough to warrant efforts to eliminate the possibility of a needle-stick injury entirely.

A wide variety of hypodermic syringes have been proposed in an attempt to prevent needle-stick injuries. These structures generally require modification of the syringe barrel. For example, U.S. Pat. No. 4,737,144 to Choksi discloses a syringe with a sleeve which can be locked in a retracted position and also an extended position. The locking mechanism includes a slot formed near the end of the barrel which cooperates with spring urged tabs on the sleeve.

U.S. Pat. No. 4,425,120 to Sampson, et al., discloses a needle guard mounted on the barrel of the syringe. The guard can be releasably locked in the retracted position or locked in the extended position. Locking of the guard is effected by a track on the internal surface of the guard and track-engaging members on the barrel.

U.S. Pat. No. 4,573,976, also to Sampson, et al., discloses a similar structure with different locking means.

U.S. Pat. No. 4,356,822 to Winstead-Hall discloses a syringe assembly having a barrel and tubular guard with multiple locking members provided for securing the barrel and cap in a number of relative axial positions. A frangible end closure may be provided on the end of the cap closest to the needle. The locking members permit different locked positions for exposing different amounts of the needle.

Another approach is to provide a shield integral with the needle instead of the barrel. U.S. Pat. No. 3,134,380 to Armano discloses a collapsible needle guard integral with the needle portion of the syringe. The needle with guard is assembled and sterilized by the manufacturer. The purpose of the guard is to shield the needle from the view of the patient.

None of these structures are known to be in widespread use. Most standard hypodermic syringe assemblies presently in use are unshielded and do not resolve the problem of needle sticks.

SUMMARY OF THE INVENTION

Briefly, the present invention comprises an improved needle guard that is compatible with the typical, unguarded hypodermic syringes with permanently mounted needles, currently in use. The invention also comprises a method to prevent needle stick injuries. The needle guard is simple to use, inexpensive, does not require modification of the syringe in any way, and is effective to prevent needle-stick injuries. The needle guard places an irreversible fixed barrier between the hands of the syringe user and the point of the needle after use. It permits the hands of the user to remain behind the needle as it is covered.

The needle guard includes a fitting or bushing cooperative with the barrel of the syringe and a slidable, protective sleeve which is retained on the fitting. A packaging cap and packaging body may also be provided as optional features. The fitting deformably mounts on the syringe barrel by cutting into the surface of the needle hub portion of the barrel. The fitting is then used to support the slidable protective sleeve.

In one method of assembling the needle guard onto the syringe, the fitting is slidably placed inside of the sleeve, and the packaging cap is placed over one end of the protective sleeve. The user grasps the needle guard and orients the needle guard so that the open end of the protective sleeve faces the user. The user then slides the syringe barrel into the open end of the protective sleeve, while simultaneously holding the packaging cap on the other end of the sleeve. The syringe will contact the fitting which abuts an internal shoulder in the packaging cap. The shoulder provides the means to provide a counter-force against the syringe whereby the needle hub portion of the syringe deformably engages with a bushing contained within the sleeve. The needle will then extend from the bushing and protrude from the sleeve into the protective packaging cap. The packaging cap may then be removed so the hypodermic syringe is fully assembled with the needle guard sleeve in the retracted position so that the needle is exposed and ready for use.

After use, the user grasps the protective sleeve and pushes it forward along the barrel in the direction of the needle. The user slides the sleeve forward until the bushing and sleeve irreversibly lock. The sleeve of the needle guard now extends beyond the pointed tip of hypodermic needle preventing access to the contaminated needle and thus preventing needle stick by the needle. Note, very importantly that the user of the syringe operates the sleeve from a position behind the needle point and thereby avoids exposure of the operator's hand to a needle stick when moving the sleeve forward over the needle. Similarly, the protective cap is removed by withdrawing it from the needle in a manner which requires the operator to remove the cap in a direction moving away from the needle point.

The present invention is a substantial improvement relative to the prior art because it is convenient and practical. Accordingly, it is an object of this invention to provide an improved syringe construction which prevents needle-stick injuries and that is easy to use.

Another object of the invention is to provide an improved syringe construction which is both safe and effective.

Yet another object of the invention is to provide a needle guard that is inexpensive, easily manufactured, and is useful with existing syringe constructions.

An additional object of this invention is to provide a simple needle guard construction for use with syringes having permanently mounted needles.

A further object of this invention is to provide a simple method for preventing needle stick injuries on standard syringes.

Other objects and advantages of the invention will become apparent from the following description of the invention.

BRIEF DESCRIPTION OF THE DRAWINGS

In the detailed description which follows, reference will be made to the drawings comprised of the following figures:

FIG. 1 is a perspective view of a first embodiment of the present invention, showing the needle guard with a packaging cap and packaging body;

FIG. 2 is an exploded isometric view of the embodiment of FIG. 1 of the present invention showing the packaging cap, bushing, and a sleeve;

DESCRIPTION OF THE PREFERRED EMBODIMENTS

Figure 2A:
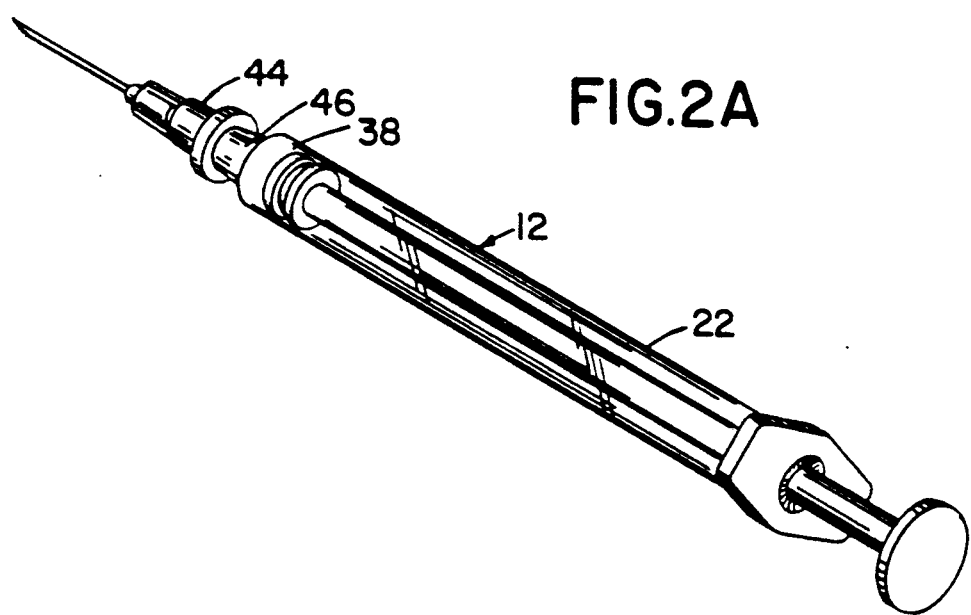
FIG. 2A is a perspective view of a standard hypodermic syringe with a removable needle.

The present invention provides a unique and straightforward construction and method to prevent needle-stick injuries resulting from use of currently available syringes. Some standard hypodermic syringes, such as syringe 12 of FIG. 2A, have detachable needles 44. For illustration purposes, syringe 12 is shown fully assembled in the ordinary fashion. Other commercially available hypodermic syringes, such as syringe 13 of FIG. 2B, have a unitary construction, so that the needle 43 is permanently mounted on the barrel 25 of the syringe 13.

Figure 2B:
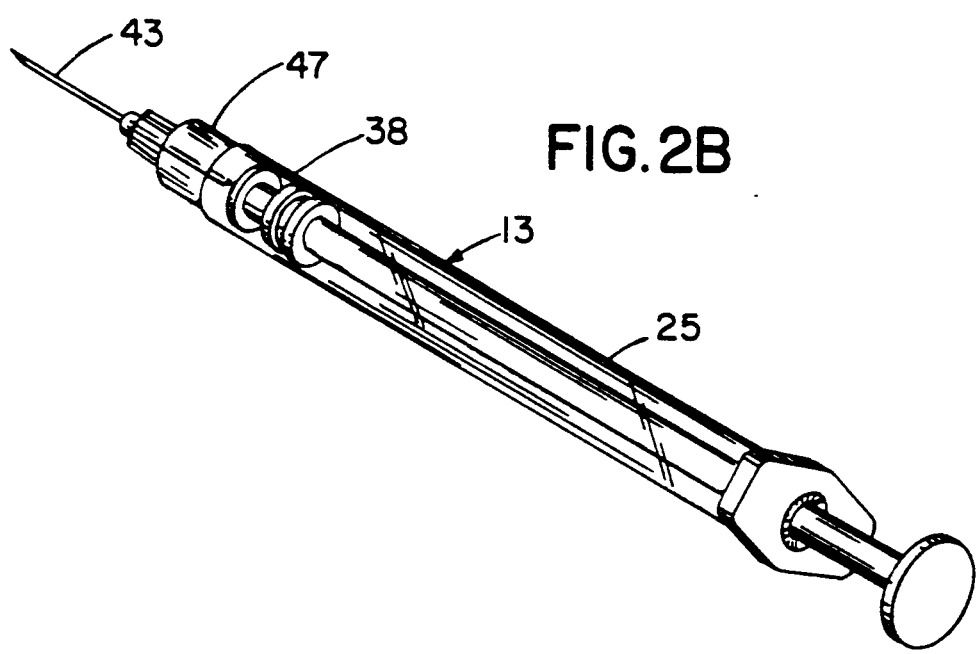
FIG. 2B is a perspective view of a standard hypodermic syringe with a permanently mounted needle.

The embodiment of the invention in FIGS. 1 and 2 may be used with the permanently mounted type of syringe 13 shown in FIG. 2B. The invention comprises an appliance for combination with standard syringes commonly in use. The needle guard 10 is comprised of a protective sleeve 14 and a fitting or bushing 16, as well as an optional packaging cap 18 and optional packaging body 19. The needle guard 10 is mounted on the syringe 13, used therewith, and then the assembly is discarded. When the needle guard 10 is positioned upon the syringe 13, the bushing 16 deformably fits on the needle hub portion 47 of the barrel 25 of the syringe 13 and slidably retains the sleeve 14. Sleeve 14 is slidable between a retracted, needle exposed position and an irreversible extended needle protective or covered position.

The optional packaging cap 18 is comprised of a first portion 21 and a second portion 27, both portions being hollow and generally cylindrical in shape. First portion 21 is sealed at its top end by wall 48. The bottom end of first portion 21, opposite the top end, is open. Thus, first portion 21 defines a space in which a portion of a hypodermic needle may be disposed.

Referring to FIG. 2, the top end of second portion 27 is connected to the bottom end of first portion 21, thus defining an internal annular shoulder 29. First portion 21 and second portion 27 may be joined by any common means known in the art, or may be molded together as an integral unit. The bottom end of second portion 27, opposite the top end, is open, and defines a space that may slidably cooperate with the exterior surface of sleeve 14.

Referring again to FIG. 2, the protective sleeve 14 is a hollow, molded plastic cylindrical tube. In the alternative, the sleeve 14 might have another shape, with an oval or polygonal cross section, for example, so long as its interior cross section is adequate to admit the barrel 25 of the syringe 13 and is cooperative with the bushing 16. Sleeve 14 includes guide means keyed to the bushing 16. In FIGS. 1 and 2, the guide means comprise straight longitudinal ribs 24a and 24b on the interior surface of sleeve 14, which coact with grooves 26a and 26b on the exterior surface of bushing 16 to prevent rotation of the sleeve 14 relative to bushing 16.

Sleeve 14 also has means to limit axial movement of sleeve 14 relative to bushing 16, including two depressions or recesses 28a and 28b, located on the interior surface of sleeve 14 at its distal end near the packaging cap 18. Recesses 28a and 28b, spaced about 180° apart, are adapted to reversibly engage radially outwardly extending members of fitting 16 such as lugs or tangs 30a and 30b when the sleeve 14 is in the retracted, needle exposed position. Tangs 30a and 30b are biased radially outwardly, extend axially from the distal end of bushing 16 in the direction of the needle 43, and have the form of cantilever elastic members or beams. Tangs 30a and 30b terminate with radially outwardly extending lips or ridges 42a and 42b, respectively, that reversibly engage in recesses 28a and 28b or irreversibly engage with slots 34a and 34b in sleeve 14 as described below. Note, the recesses 28a, 28b serve to retain the lips 42a, 42b in a manner which does not apply stress or strain to the tongs 30a, 30b so that the tongs 30a, 30b will retain their elasticity. Lips 42a, 42b thus fit into the recesses 28a, 28b and the sides of the recesses 28a, 28b are sloped to permit the lips 42a, 42b to move out or be "cammed" out of the recesses upon application of axial force to the sleeve 14.

Means for irreversibly locking the needle guard 10 in the extended position are also provided on sleeve 14. As disclosed in FIGS. 1 and 2, such means comprise axial slots 34a and 34b located near the proximal end of sleeve 14, which are adapted to receive and irreversibly lock with the tangs 30a and 30b, and more particularly, the lips 42a and 42b of bushing 16. It has been found that axial orientation of the tangs 30a and 30b in the direction of the needle 43 (as shown in FIG. 2) provides superior locking force for limiting axial movement of the sleeve 14 in the direction opposite of the needle 43 when the sleeve 14 is in the extended position. For limiting axial movement of sleeve 14 on the bushing 16 in the direction of the needle 43, sleeve 14 has a shoulder or an inwardly extending flange 32 at its proximal end. In this manner both the translational and rotational motion of the bushing 16 within the sleeve 14 is controlled during use of the hypodermic syringe 13 and needle guard 10.

The fitting or bushing 16 has a generally annular shape with an exterior cylindrical surface 35 adapted to slidably cooperate with the interior surface of sleeve 14. Fitting 16 has an interior cylindrical surface 36 adapted to slidably cooperate with the syringe barrel 25. Interior surface 36 of bushing 16 contains a deformable engagement means adapted to cooperatively mount bushing 16 in a fixed position on syringe barrel 25. In FIG. 2, the deformable engagement means is comprised of radially inwardly extending retaining flange 40 proximate the distal end of bushing 16. Flange 40 defines a sharp, interior annular tapered surface or edge 41, provided to prevent the barrel 25 from being pushed through the bushing 16 entirely, and, as described below, to deformably engage syringe barrel 25. Retaining flange 40 is manufactured from a material that has a harder composition than the material composing needle hub 47 of syringe 13.

Bushing 16 preferably has two engageable members or tangs 30a, 30b, spaced about 180° from one another on the circumference of bushing 16 and cooperative with respective detention depressions 28a, 28b and slots 34a, 34b, on the inside of axially slidable sleeve 14. The lips 42a, 42b of tangs 30a and 30b thus reversibly engage depressions 28a and 28b of sleeve 14 when the sleeve 14 is in the retracted position to thereby hold sleeve 14 in place. When the sleeve 14 is slid in the direction of the needle 43 into the extended position, detent lips 42a, 42b irreversibly engage slots 34a, 34b spaced about 180° apart. Whether the lips 42a, 42b reversibly or irreversibly engage the sleeve 14 depends on the depth and shape of the engaging configuration of sleeve 14. Thus, slots 34a, 34b have a depth and shape that insures that lips 42a, 42b are fully and irreversibly engaged. Depressions 28a, 28b only partially engage lips 42a, 42b and this engagement can be overcome by a mild axial force.

The needle guard 10 may be provided as an "add-on" product, i.e., to be manually attached to a syringe separately obtained by the user. For assembly and packaging purposes, the bushing 16 will be slidably disposed within sleeve 14, by placement through the distal end of the sleeve 14 proximate the packaging cap 18. The distal portion of the sleeve-bushing combination slidably fits within the space defined by second portion 27 of packaging cap 18. Furthermore, as shown in FIG. 1, the assembled cap-sleeve-bushing unit slidably fits within packaging body 19 as an added measure of protection and cleanliness during shipment and use of the assembly. The generally cylindrical shape of packaging cap 18 cooperates with the generally conical shape of packaging body 19 to form a releasable, frictional fit between the cap 18 and the body 19.

To attach the needle guard onto the syringe, the user slidably removes the packaging body 19 from the needle guard assembly. With the packaging cap 18 still in place, the user slides syringe barrel 25 into the proximal end of sleeve 14 through the opening formed by shoulder 32 in protective sleeve 14. The needle hub portion 47 of syringe barrel 25 will eventually engage the retaining flange 40 of bushing 16. At this point, needle 43 will have passed through retaining flange 40 as needle hub 47 is pushed into contact with the interior edge 41 of flange 40. A portion of needle 43 will be disposed within packaging cap 18.

As can best be seen in FIG. 2, as the needle hub 47 of syringe barrel 25 engages the interior edge 41 of flange 40, the bushing 16 will be forced in the direction of the packaging cap 18. However, tangs 30a, 30b will abut interior shoulder 29 of packaging cap 18, providing a counter-force, opposite in direction to the movement of the syringe 25. This counter-force may be maintained when the user grasps the cap 18 with his or her other hand.

The movement of the syringe 25 now being stopped, continued application of force to the syringe 25 results in the interior edge 41 of flange 40 cutting into and penetrating the needle hub 47 of syringe barrel 25, due to the relative hardness of the flange 40 and syringe barrel 25 as noted above. The penetration of flange 40 into the surface of the needle hub 47 deformably and permanently affixes the bushing 16 to the syringe 13.

Figure 2D:
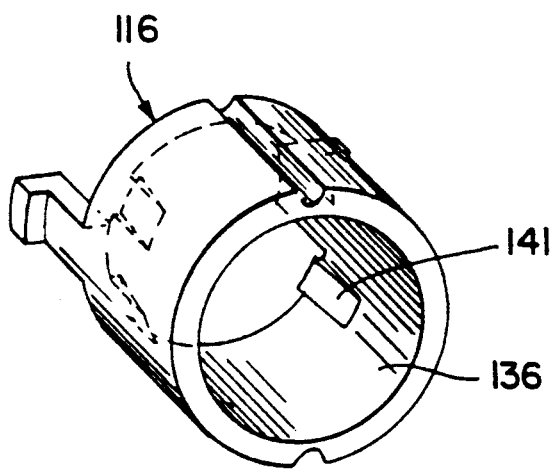
FIG. 2D is a perspective view of one embodiment of a bushing.

In the preferred embodiment shown in FIG. 2D, the uniform annular retaining flange 40 is replaced with a series of sharp axial ridges 141 distributed about the circumference of the interior surface 136 of bushing 116, near the distal end of bushing 116. The ridges 141 are shaped generally as inclined planes, the ridges being inclined inwardly from the interior surface 136 in the radial direction. As with the uniform flange 40, the ridges 141 are manufactured from a material that is harder than the material from which the needle hub 47 is manufactured, thus allowing the ridges to penetrate and engage needle hub 47, as described above. In the preferred embodiment, the ridges 141 are made of an acrylic material, whereas the typical syringe barrel is made of polypropylene or polyethylene. The series of sharp ridges 141 has been found to be superior to the uniform flange 40, due to variations in the size of the needle hub 47 that occur during syringe manufacturing.

Figure 2C:
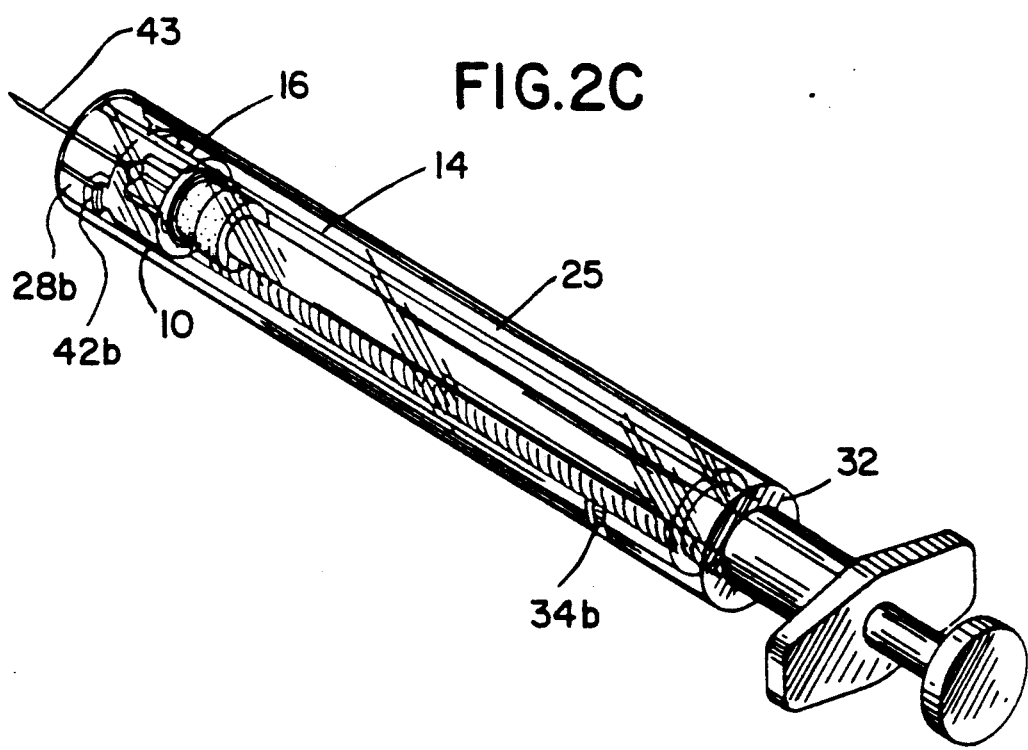
FIG. 2C is a perspective view of a needle guard mounted on a standard hypodermic syringe with a permanently mounted needle.

When the needle guard 10 has been deformably affixed to the syringe barrel 25, the user removes the packaging cap 18, to expose the needle 43, now ready for use, as shown in FIG. 2C. After using the syringe and needle to inject a fluid into a patient, or to draw a sample of a fluid from a patient, the user grasps the sleeve 14 and pushes it axially forward, towards the needle 43, breaking the engagement between lips 42a, 42b and depressions 28a, 28b. The user slides the sleeve 14 until detent members 42a, 42b irreversibly engage slots 34a, 34b and shoulder 32 abuts bushing 16. The distal end of sleeve 14 now extends beyond the tip of contaminated needle 43, preventing any accidental injuries. The protected syringe may then be disposed of as a unit.

As can now be seen, before, during and after use of the needle guard-syringe combination the user's hands are, at all times, kept a safe distance away from the needle 43. Before use, (during assembly) the each of the user's hands is either safely behind the needle 43, or at a distance forward of the needle 43, separated by the length of the protective sleeve 14. During use of the syringe 12, the user's hands are again, either behind the needle 43, or grasping the sleeve 14 for support during injection/drawing. Finally, after use of the syringe 12, instead of placing a cap over the used syringe 12 and exposing the user to the danger of placing his or her hands near the contaminated needle 43, the user's hands remain safely behind the needle as the protective sleeve 14 is slid until it irreversibly extends beyond the tip of the needle, permanently preventing further access thereto.

As an alternative to providing the needle guard 10 as an "add on" product, the needle guard 10 may be provided already affixed to a syringe 13. In this embodiment, the needle guard 10 may be affixed to the syringe barrel 25 by mechanized means, as opposed to the manual method described above. The packaging cap 18 is not used during the mechanized assembly process. Instead, a machine containing a mold in the shape of the packaging cap 18 is used to supply the counter-force necessary to deformably engage the needle guard onto the syringe barrel 25 as described above. This pre-assembled embodiment may be more convenient for health care workers.

Figure 3:
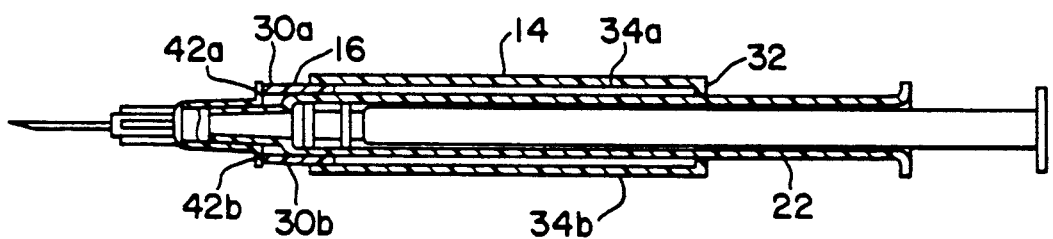
FIG. 3 is a sectional view of a syringe and a second embodiment of the present invention in the retracted position.
Figure 4:
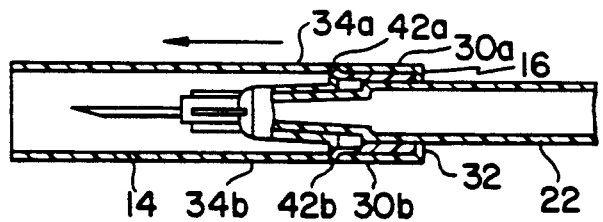
FIG. 4 is a partial sectional view of the second embodiment of the needle guard mounted on a hypodermic syringe with the sleeve in a locked, extended position.

Turning now to FIGS. 3 and 4, a second embodiment of the present invention is depicted. In FIG. 3 the protective sleeve 14 is in the retracted position, and in FIG. 4 it is in the locked extended position. The interior surface 36 of bushing 16 is engaged with the lead portion 23 of the exterior surface of the syringe barrel 22. The distal end of the bushing 16 includes tangs 30a, 30b identical to the construction of the first embodiment. However, the second embodiment does not have the depressions 28a, 28b on the inside surface of the sleeve 14 as does the first embodiment so tangs 30a, 30b are not engaged. Thus as shown in FIG. 3, sleeve 14 is free to slide along bushing 16 and may be retracted to the point where it may lose contact with the bushing 16. However, as shown in FIG. 4, when sleeve 14 is moved to cover the needle, sleeve 14 is retained in position by tabs 42a, 42b, which are engaged with slots 34a, 34b of the sleeve 14 and also by shoulder 32 which abuts the proximate end of bushing 16. The shoulder 32 acts to limit slidable motion of the sleeve 14 on the bushing 16 and syringe when the sleeve 14 is moved to cover or protect the needle. (See FIG. 4). The shoulder 32 may be eliminated without departing from the spirit of the invention since the cooperative tabs 42a, 42b and slots or radial openings 34a, 34b in the sleeve 14 irreversibly lock the sleeve 14.

Figure 5:
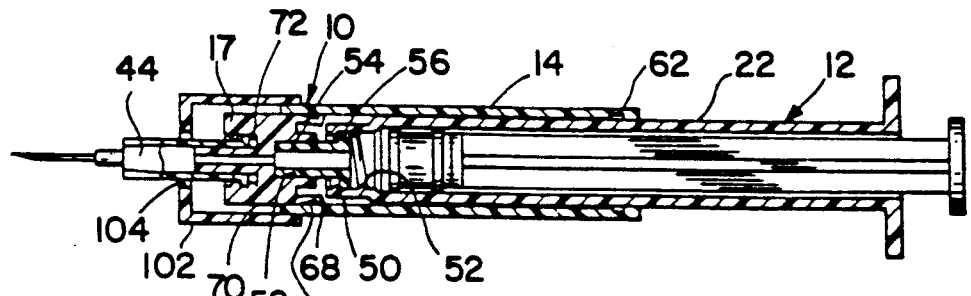
FIG. 5 is a sectional view of a third embodiment of the present invention, showing the hypodermic syringe with a needle guard mounted between the hypodermic syringe and the hypodermic needle, in the retracted position.
Figure 6:
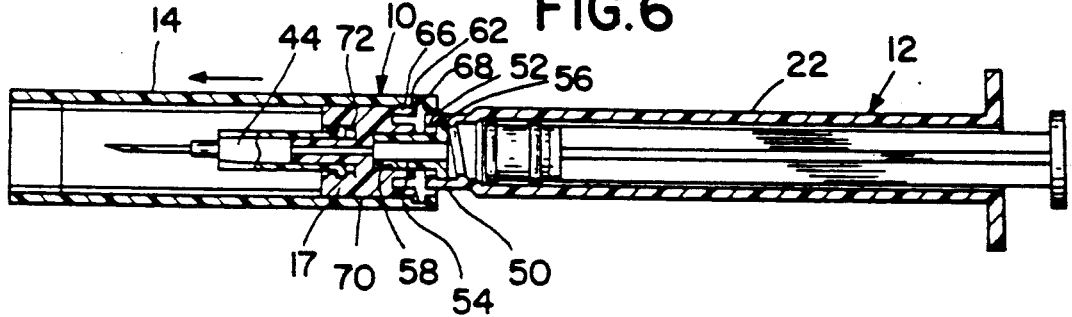
FIG. 6 is a sectional view of the third embodiment of the present invention with the sleeve in the locked extended position.
Figure 7:
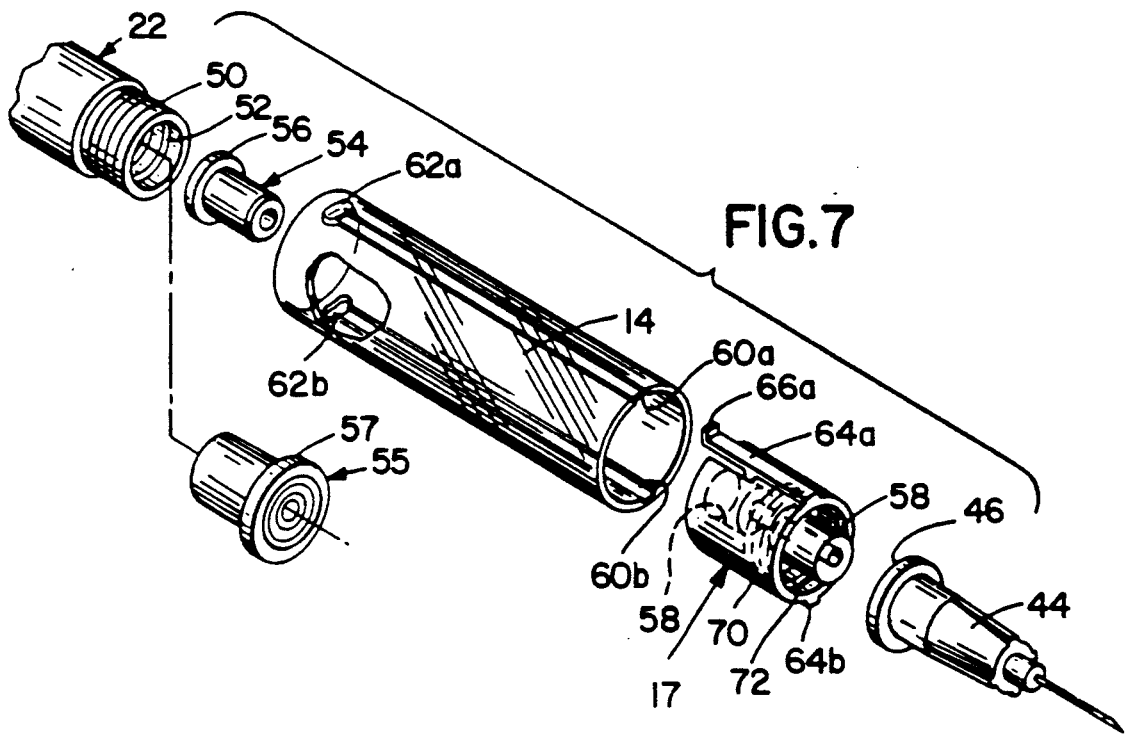
FIG. 7 is an exploded isometric view of the third embodiment of the present invention showing the hypodermic syringe barrel, sleeve, bushing, and hypodermic needle.

FIGS. 5-7 disclose a third embodiment of the present invention, wherein like elements are given the same designations. The standard hypodermic syringe 12 in FIGS. 5-7 has a threaded connection between the barrel 22 and the needle hub 44, as opposed to the frictional fit exemplified in FIGS. 1-4. The barrel 22 thus includes a projecting tube, connector or nipple 50 at one end which includes internal threads 52. The internal threads 52 normally cooperate with the thread form or thread flange 46 of needle hub 44. In the embodiment of FIG. 7, however, bushing 17 is combined with a hollow tube member 54 having a thread form 56 or thread flange 56. The member 54 and bushing 17 together define a total bushing assembly which connects tube 50 with hub 44 while supporting sleeve 14.

The bushing 17 thus comprises a cylindrical external tube 70 with the cylindrical internal member 54 fitted or welded into counterbore 58. The flange 56 of member 54 cooperates with threads 52 of tube 50 so that the bushing assembly can be threadably mated with tube 50. The external tube 70 and internal tube member 54 are joined internally of tube 70. Bushing 17 and member 54 may be a unitary, single molded piece.

Molded within tube 70 is a forward frustoconical section 58a which is designed to guide and receive the compatible opening of needle hub 44. The hub 44 includes a thread flange 46 which may be threaded with compatible threads 72 on the forward inside end of tube 70 of bushing 17. Note, a centerline passage for fluid flow is defined through tube 50, member 54, section 58a and hub 44 to the needle.

Sleeve 14 has internal, longitudinal grooves 60a, 60b with recesses 62a, 62b near the proximal end of sleeve 14. Bushing 17 rearwardly extending ribs 64a, 64b each terminating in tangs 66a, 66b respectively, and each having outwardly extending tabs or lips 68a, 68b on the outside. Lips 68a, 68b ride in grooves 60a and 60b when the needle guard sleeve 14 is in the retracted position of FIG. 5. In the fully extended position of FIG. 6, lips 68a, 68b are forced or bias into recesses 62a, 62b, thereby locking sleeve 14 against further longitudinal movement. In the alternative, grooves 60a, 60b and recesses 62a, 62b may be replaced by a gradually diminishing depth slot such that ribs 64a, 64b are tightly, irreversibly wedged in the slots when the sleeve 14 is slid into the extended position.

After use, the needle hub 44 of this embodiment may be removed from the barrel 22 along with the needle guard sleeve 14 for disposal. The user merely grasps sleeve 14 and twists and pulls the assembly, thereby unscrewing and removing the hollow bushing 17 with member 54, sleeve 14 and hub 44.

If the hollow sleeve 14, brushing 17 and needle hub 44 are removed, a stopper 55 may be pushed into the open tube 50. Thus, the barrel 22 and any contents of the barrel, such as blood samples drawn from a patient, are left in tact and sealed by stopper 55 with a flange 57.

FIG. 5 illustrates another feature of the invention useful with large capacity syringes, e.g., 5 c.c. or 6 c.c. syringes. Because the diameter of the sleeve 14 for such large capacity syringes is relatively high, an operator may accidentally place their finger in the open end and contact a protected needle. To avoid such an event, a protective cap 102 with a restricted diameter opening 104 fits over the sleeve 14 and is attached thereto for movement therewith. The opening 104 permits the needle to pass therethrough, but prevents access by a finger, for example.

Figure 8:
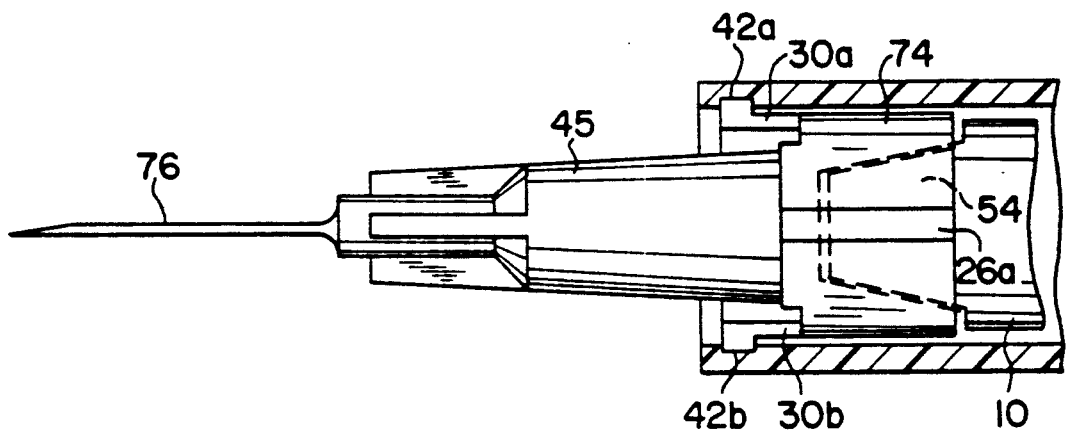
FIG. 8 is a sectional view of a fourth embodiment of the present invention, showing a hypodermic needle with a fitting or bushing formed as an integral part of the needle support.
Figure 9:
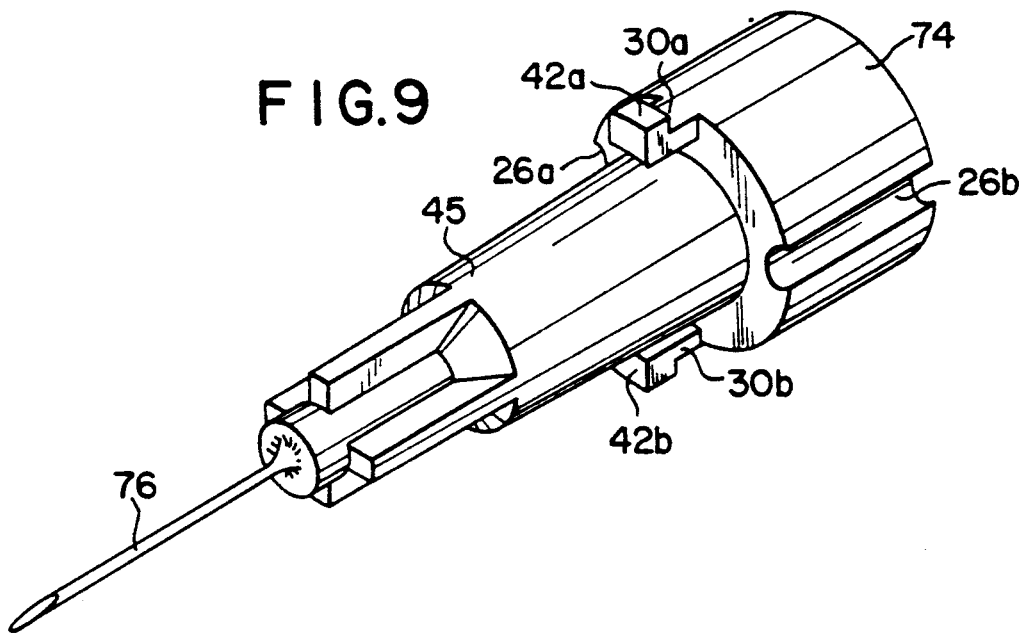
FIG. 9 is a perspective view of the fourth embodiment of the present invention, showing a hypodermic needle with the fitting formed as an integral part of the needle support.

Turning now to FIGS. 8 and 9, an alternative combination integral needle and bushing 45 is disclosed. It is formed with a base 74 having an outer configuration corresponding to that of bushing 16. The needle 76 is pre-packaged with the protective sleeve 14 in the retracted position by the manufacturer. The needle 76 is housed within the packaging cap 18 for storage and shipment. The needle base 74 can cooperate with the sleeve 14 illustrated in FIGS. 1-7. The needle base 74 can cooperate with the sleeve 14 illustrated in FIGS. 1-7. Thus, the needle base 74 has a generally annular shape with an exterior cylindrical surface adapted to fit within the interior surface of sleeve 14. Needle base 74 has grooves 26a, 26b which are capable of coacting with longitudinal ribs 24 on the interior surface of sleeve 14, and lugs or tangs 30a, 30b which terminate with lips 42a, 42b and are capable of engaging both recesses 28a, 28b of sleeve 14 and also slots 34a, 34b of sleeve 14 as described above. In other words a bushing and needle construction are integrally molded as a single unit in the embodiment of FIGS. 8 and 9.

Although exemplary embodiments of the invention have been shown and described, many changes and substitutions may be made by one of ordinary skill in the art without departing from the scope of this invention. For example, although the sleeve is disclosed to be fully or partially translucent, it may be readily seen that the sleeve could be made of opaque materials except for a window or slot which allows the measure of the syringe to be read. In other applications, where it is not necessary to read a direct measurement off a syringe barrel, the shield may be completely opaque. This invention is suited for use with any medical or industrial instrument, such as intravenous needles or catheters, or other instruments which have a sharp point or blade. Other versions of this needle guard may be adapted for use with other types of syringes and medical implements without departing from the scope of this invention. This invention therefore includes alternatives to the specific configurations described in the exemplary embodiments and is limited only to the language of the claims.

What is claimed is:

1. A needle guard for a hypodermic syringe assembly, the assembly being of the type including a hypodermic needle and a syringe barrel having a needle hub portion adjacent the hypodermic needle, the needle guard comprising a separate assembly which is attachable to the syringe assembly and which in combination therewith maintains either a non-protective or an irreversible protective configuration for the needle, said needle guard comprising in combination:

a separate, attachable fitting having an exterior portion and an interior portion, the interior portion having deformable engagement means adapted to cooperatively mount the fitting in a fixed position on the needle hub portion of the syringe, the deformable engagement means including means to penetrate the surface of the needle hub portion of the syringe;

a hollow protective sleeve on the fitting, said sleeve having an interior surface adapted to slidably coact with the fitting, an exterior surface, a distal end and a proximal end;

guide means for slidably connecting the interior surface of said sleeve and the exterior portion of said fitting, said sleeve thereby being movable on the fitting axially in the direction of the length of the needle between a non-protective retracted position exposing the needle and a protective, extended position covering the needle; and means for irreversibly locking said sleeve only in the protective, extended position relative to said fitting, whereby axial and rotational movement of the sleeve relative to the fitting is prevented, and the sleeve in the protective, extended position protrudes beyond the tip of the needle such that the sleeve defines a guard which irreversibly prevents further access to the needle once the sleeve has been moved to the extended position.

2. A needle guard according to claim 1 wherein the deformable engagement means is comprised of an annular flange proximate the distal end of the fitting.

3. A needle guard according to claim 2 wherein the annular flange defines a sharp, interior annular tapered surface, and the annular flange is composed of a material that is harder than the material from which the needle hub is composed.

4. A needle guard according to claim 3 wherein the flange is composed of an acrylic material.

5. A needle guard according to claim 1 wherein the deformable engagement means is comprised of a series of sharp axial ridges distributed about the circumference of the interior surface of the fitting, and the ridges being composed of a material that is harder than the material from which the needle hub is composed.

6. A needle guard according to claim 5 wherein the ridges are shaped generally as inclined planes, the ridges being inclined inwardly in the radial direction.

7. A needle guard according to claim 6 wherein the ridges are composed of an acrylic material.

8. A needle guard according to claim 1, 2, 3, 4, 5, 6, or 7 wherein the means for irreversibly locking the sleeve in the extended position is comprised of at least one elastic axial rib located on the exterior surface of the fitting and terminating with an outwardly extending tang, the tang being biased radially outward by the rib to engage the sleeve, and the sleeve adapted to irreversibly engage the tang when the sleeve is axially positioned in the extended position.

9. A needle guard according to claim 8 wherein the rib extends axially from the fitting in the direction of the needle.

10. A needle guard according to claim 9 wherein the means for irreversibly locking the sleeve in the extended position further comprises a depression on the interior surface of the sleeve near the distal end of the sleeve adapted to reversibly frictionally engage the tang, and a slot in the sleeve near the proximal end of the sleeve adapted to irreversibly frictionally engage the tang.

11. A needle guard for a hypodermic syringe with a permanently mounted needle, the hypodermic syringe of the type having a needle hub portion proximate the needle, the needle guard comprising a separate assembly which is attachable to the hypodermic syringe and which in combination therewith maintains either a non-protective or an irreversible protective configuration for the needle, said needle guard comprising in combination:

a separate, attachable fitting having an exterior portion and an interior portion, the interior portion having deformable engagement means adapted to cooperatively mount the fitting in a fixed position on the needle hub portion of the syringe, the deformable engagement means including means to penetrate the surface of the needle hub portion of the syringe;

a hollow protective sleeve on the fitting, said sleeve having an interior surface adapted to slidably coact with the fitting, an exterior surface, a distal end and a proximal end, said sleeve thereby being movable on the fitting axially in the direction of the length of the needle between a non-protective retracted position exposing the needle and a protective, extended position covering the needle;

a hollow, generally cylindrical packaging cap being adapted to slidably cooperate with the distal end of the sleeve, the cap defining an internal annular shoulder; and means for irreversibly locking said sleeve only in the protective, extended position relative to said fitting, whereby axial and rotational movement of the sleeve relative to the fitting is prevented, and the sleeve in the protective, extended position protrudes beyond the tip of the needle such that the sleeve defines a guard which irreversibly prevents further access to the needle once the sleeve has been moved to the extended position.

12. A needle guard according to claim 11, wherein the deformable engagement means is comprised of an annular flange proximate the distal end of the fitting.

13. A needle guard according to claim 12, wherein the annular flange defines a sharp, interior annular tapered surface, and the annular flange is composed of a material that is harder than the material from which the needle hub is composed.

14. A needle guard according to claim 13 wherein the flange is composed of an acrylic material.

15. A needle guard according to claim 11 wherein the deformable engagement means is comprised of a series of sharp axial ridges distributed about the circumference of the interior surface of the fitting, and the ridges being composed of a material that is harder than the material from which the needle hub is composed.

16. A needle guard according to claim 15 wherein the ridges are shaped generally as inclined planes, the ridges being inclined inwardly in the radial direction.

17. A needle guard according to claim 16 wherein the ridges are composed of an acrylic material.

18. A needle guard according to claim 11, 12, 13, 14, 15, 16, or 17 wherein the means for irreversibly locking the sleeve in the extended position is comprised of at least one elastic axial rib located on the exterior surface of the fitting and terminating with an outwardly extending tang, the tang being biased radially outward by the rib to engage the sleeve, and the sleeve adapted to irreversibly engage the tang when the sleeve is axially positioned in the extended position.

19. A needle guard according to claim 18 wherein the rib extends axially from the fitting in the direction of the needle.

20. A needle guard according to claim 19 wherein the means for irreversibly locking the sleeve in the extended position further comprises a depression on the interior surface of the sleeve near the distal end of the sleeve adapted to reversibly frictionally engage the tang, and a slot in the sleeve near the proximal end of the sleeve adapted to irreversibly frictionally engage the tang.

21. A method to prevent needle stick injuries caused by a hypodermic syringe of the type including a hypodermic needle and a syringe barrel, the method comprising the steps of:
(a) inserting a fitting into a protective sleeve, the fitting being adapted to cooperatively mount on a hypodermic syringe;
(b) sliding the sleeve into a packaging cap;
(c) guiding a hypodermic syringe into the sleeve;
(d) applying an axial force to the syringe in the direction of the cap, while simultaneously applying an axial counter-force to the cap, so the fitting engages the syringe;
(e) removing the packaging cap from the sleeve;
(f) forcing a fluid through the syringe needle;
(g) sliding the sleeve in the direction of the needle so the sleeve irreversibly extends beyond the tip of the needle.

22. A method to prevent needle stick injuries caused by a hypodermic syringe of the type including a hypodermic needle and a syringe barrel, the method comprising the steps of:
(a) inserting a fitting into a protective sleeve, the fitting being adapted to cooperatively mount on a hypodermic syringe;
(b) sliding the sleeve into a machine mold;
(c) guiding a hypodermic syringe into the sleeve;
(d) supplying an axial force to the syringe in the direction of the mold, while simultaneously applying an axial counter-force from the mold, so the fitting engages the syringe;
(e) removing the sleeve from the mold;
(f) forcing a fluid through the syringe needle;
(g) sliding the sleeve in the direction of the needle so the sleeve irreversibly extends beyond the tip of the needle.

* * * * *